United States Patent
Cropper et al.

(10) Patent No.: US 8,814,901 B2
(45) Date of Patent: Aug. 26, 2014

(54) SURGICAL FASTENER

(75) Inventors: Michael S. Cropper, Edgewood, KY (US); Richard C. Smith, Milford, OH (US); John P. Measamer, Cincinnati, OH (US); Richard F. Schwemberger, Cincinnati, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 1260 days.

(21) Appl. No.: 11/745,835

(22) Filed: May 8, 2007

(65) Prior Publication Data

US 2008/0281354 A1  Nov. 13, 2008

(51) Int. Cl.
*A61B 17/08* (2006.01)

(52) U.S. Cl.
USPC .......................................... 606/220; 606/151

(58) Field of Classification Search
USPC ........... 606/75, 116, 117, 219–221, 294, 296; 24/170, 493, 350, 358, 366, 367.1, 24/368, 334, 327
See application file for complete search history.

(56) References Cited

U.S. PATENT DOCUMENTS

| | | | | |
|---|---|---|---|---|
| 3,385,299 | A | * | 5/1968 | Le Roy ........................ 606/218 |
| 4,506,671 | A | * | 3/1985 | Green ........................ 227/181.1 |
| 5,047,047 | A | * | 9/1991 | Yoon ............................ 606/216 |
| 5,474,569 | A | * | 12/1995 | Zinreich et al. ............... 606/151 |
| 5,478,354 | A | * | 12/1995 | Tovey et al. .................... 606/219 |
| 5,571,125 | A | * | 11/1996 | Chadwick ..................... 606/151 |
| 6,241,748 | B1 | * | 6/2001 | Adams .......................... 606/220 |
| 6,273,903 | B1 | * | 8/2001 | Wilk ............................. 606/219 |
| 6,966,919 | B2 | * | 11/2005 | Sixto et al. .................... 606/153 |
| 7,033,378 | B2 | | 4/2006 | Smith et al. | 
| 7,575,389 | B2 | * | 8/2009 | Nance ........................ 403/109.2 |
| 2005/0267529 | A1 | * | 12/2005 | Crockett et al. .............. 606/215 |
| 2006/0247639 | A1 | * | 11/2006 | Anderson ........................ 606/69 |

* cited by examiner

Primary Examiner — Corrine M McDermott
Assistant Examiner — Alexander Orkin

(57) ABSTRACT

A surgical fastener for fastening tissue. The fastener includes a first piece of sheet material formed to have a generally planar base and an elongate needle portion extending upward from the base. The fastener includes a second piece of sheet material formed to have a generally planar base and an elongate needle portion extending upward from the base. The second piece of sheet material is pivotally connected to the first piece of sheet material.

6 Claims, 6 Drawing Sheets

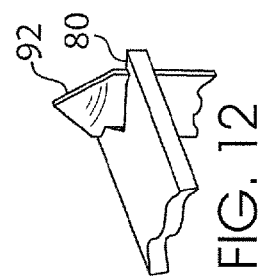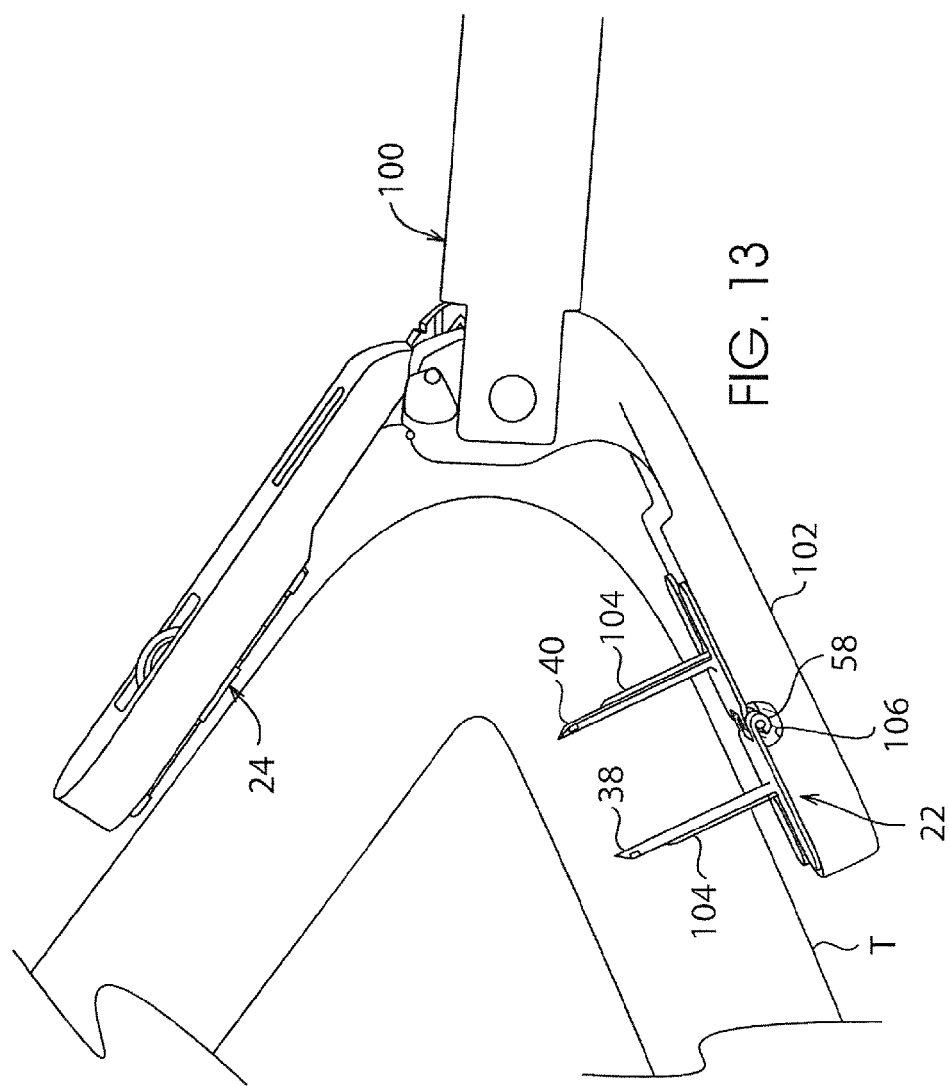

SURGICAL FASTENER

BACKGROUND OF THE INVENTION

The present invention relates generally to a surgical fastener, and more particularly to a surgical fastener having sheet metal components.

Gastroesophageal reflux disease or persistent heartburn is caused by an improper relaxation of the lower esophageal sphincter, allowing acidic stomach contents to travel into the esophagus. If left untreated, chronic reflux may cause esophageal stricture, bleeding ulcers, perforation, and scarring. Continued reflux may lead to Barrett's esophagus, involving changes in the esophageal cells and possibly leading to cancer. Antacids and proton pump inhibitors are initially used to treat this condition. If these treatments are unsuccessful, surgical intervention is often recommended.

One interventional surgical method is known as Nissen fundoplication. This procedure involves wrapping a fundus of the stomach around the lower end of the esophagus and fastening it in place to make the lower esophageal sphincter less compliant. Traditionally, this procedure was accomplished by open surgery using sutures to secure the plicated fundus of the stomach around the esophagus without penetrating the stomach. More recently, laparoscopic Nissen procedures have been used. In some laparoscopic procedures, surgical fasteners are used with an endoscopic applicator. Several different fastener designs have been developed. Some of these designs include a two piece fastener. A first of these pieces includes a base having two straight elongate needles extending perpendicularly outward from the base generally parallel to each other. A second piece includes a receiver element having openings positioned for receiving the needles of the first piece and a lock for holding the needles in place once received in the openings. In use, tissue is gathered, the needles of the first piece are pushed through the gathered tissue and the openings of the second piece to hold the tissue and fastener in place. U.S. Pat. No. 7,033,378, entitled "Surgical Fastener, Particularly for the Endoluminal Treatment of Gastroesophageal Reflux Disease (GERD)" and issued on Apr. 25, 2006, which is hereby incorporated by reference, discloses one such fastener and an applicator used with this fastener.

Although prior examples of tissue fasteners work well for their intended purpose, they can be improved by reducing their cost. Current designs require molding some components and a complex assembly process. There is a need for a fastener made by less expensive processes.

SUMMARY OF THE INVENTION

Briefly, in one aspect the present invention includes a surgical fastener for fastening tissue. The fastener comprises a first piece of sheet material formed to have a generally planar base and an elongate needle portion extending upward from the base. Further, the fastener comprises a second piece of sheet material formed to have a generally planar base and an elongate needle portion extending upward from the base. The second piece of sheet material is pivotally connected to the first piece of sheet material.

In another aspect, the present invention includes a surgical fastener for fastening tissue. The fastener comprises a base formed from sheet material having at least two pairs of opposing clips formed therein. Further the fastener includes a first latch slideably received between a first pair of the opposing clips and a second latch slideably received between a second pair of the opposing clips.

Other features of the present invention will be in part apparent and in part pointed out hereinafter.

BRIEF DESCRIPTION OF THE DRAWINGS

FIG. 12 is a detail perspective of a portion of a latch and a needle of one embodiment; and FIG. 13 is a perspective of a portion of a device for fastening the fastener to tissue.

Corresponding reference characters indicate corresponding parts throughout the several views of the drawings.

DETAILED DESCRIPTION OF THE PREFERRED EMBODIMENT

Figure 1:
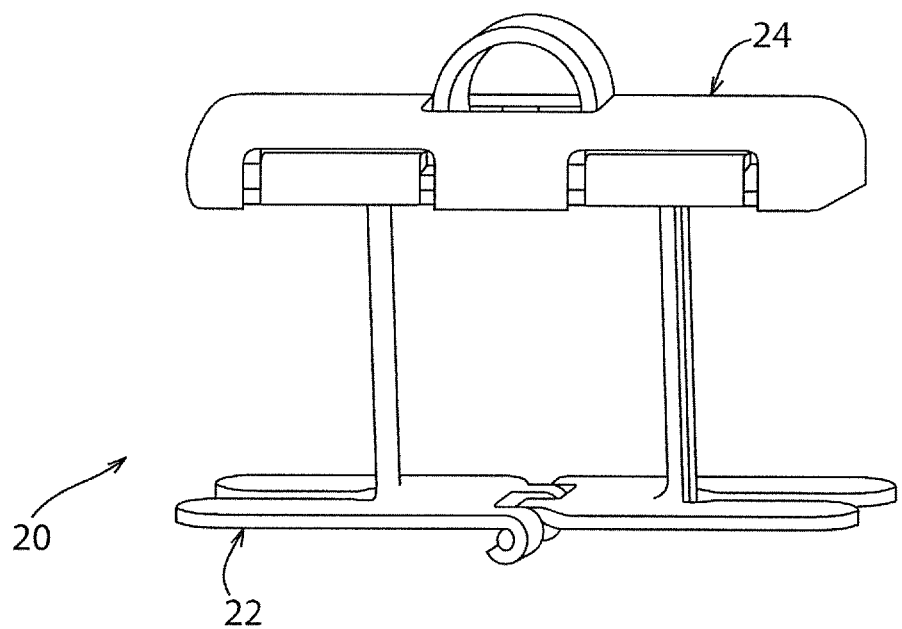
FIG. 1 is a perspective of a surgical fastener of the present invention.

Referring now to the drawings and in particular to FIG. 1, a two-piece fastener of the present invention is designated in its entirety by the reference numeral 20. The fastener 20 includes a male piece, generally designated 22, and a female piece, generally designated 24.

Figure 2:
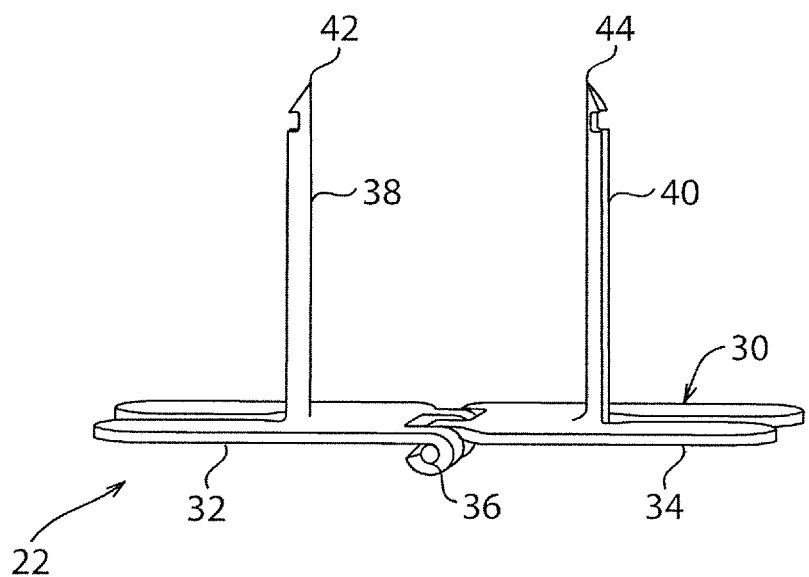
FIG. 2 is a perspective of a male piece of the fastener of FIG. 1 shown in a deployed position.
Figure 3:
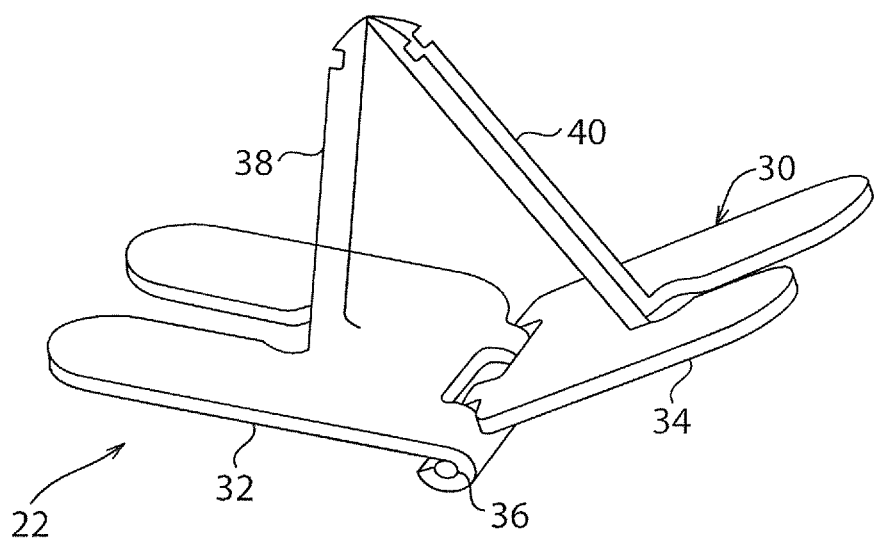
FIG. 3 is a perspective of the male piece shown in a collapsed position.

As shown in FIGS. 2 and 3, the male piece 22 includes a base, generally designated by 30, comprising two leaves 32, 34 joined by a hinge pin 36 so the male piece can move between a deployed position as shown in FIG. 2 and a collapsed position as shown in FIG. 3. Two elongate needles or posts 38, 40 extend upward from the base 30. Each of the needles 38, 40 is integrally formed with the corresponding leaf 32, 34. Although the needles 38, 40 are adapted to pierce tissue, in one embodiment they have slightly rounded tips 42, 44 so they displace tissue rather than cut tissue. The hinge pin 36 is adapted to bias the male piece 22 toward the collapsed position shown in FIG. 3 so that if the male piece becomes detached from the female piece 24 while in the patient, the male piece collapses to the collapsed position so it is less likely to pierce tissue if it moves through the body. As will be apparent to those skilled in the art, the leaves 32, 34 of the male piece may be formed from sheet material. The shape of the leaves 32, 34 may be identical. The shape of the leaves 32, 34 prior to being formed as shown in FIG. 2 will be apparent to those skilled in the art. Although the needles 38, 40 may have other dimensions without departing from the scope of the present invention, in one embodiment each needle has a length between about 0.4 inch and about 0.6 inch and a maximum width of between about 0.05 inch and about 0.06 inch. Although the base 30 may have other dimensions without departing from the scope of the present invention, in one embodiment the base, when in the fully deployed position shown in FIG. 2, has a length of between about 0.4 inch and about 0.7 inch and a width of between about 0.2 inch and about 0.4 inch.

Figure 4:
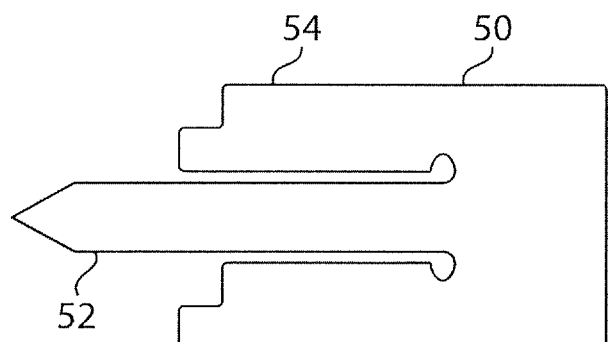
FIG. 4 is a plan of one leaf of the male piece prior to forming.
Figure 5:
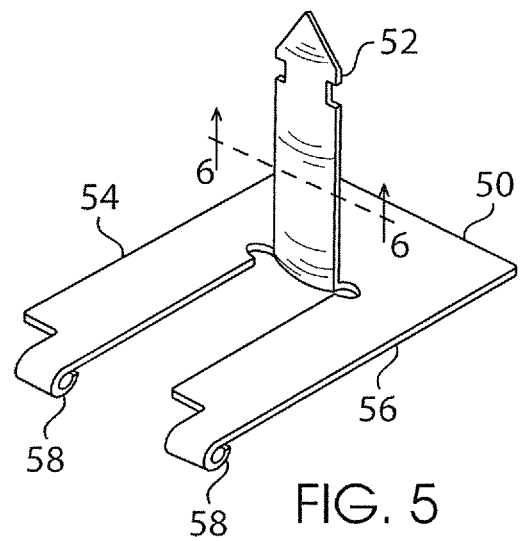
FIG. 5 is a perspective of the leaf prior to assembly.
Figure 6:
FIG. 6 is a cross section of a needle of the leaf of FIG. 5 taken through line 6-6.
Figure 7:
FIG. 7 is a cross section of a needle of an alternate design.

In an alternate embodiment, each leaf 32, 34 of the male piece 22 is formed from sheet material 50 having a shape similar to that shown in FIG. 4. A central arm 52 of the sheet material 50 is bent so it extends perpendicular to the remainder of the material as shown in FIG. 5 so it forms a needle. Ends of arms 54, 56 extending along each side of the sheet material 50 are rolled to form knuckles 58 through which a hinge pin (FIG. 2) may be inserted to join the first leaf 32 to a similarly formed leaf 34. As shown in FIG. 6, the needle (e.g., needle 38) may be bent so it has a curved cross section to provide the needle with additional rigidity. FIG. 7 shows an alternate cross-sectional needle shape. It is envisioned that the needle may have other cross-sectional shapes (e.g., a shallow V-shape, not shown) without departing from the scope of the present invention. Although the male piece 22 may be made of other materials without departing from the scope of the present invention, in one embodiment the male piece is made from titanium sheet material having a stock thickness of between about 0.010 inch and about 0.020 inch. Because the male piece 22 is formed using conventional manufacturing techniques, they will not be described in further detail.

Figure 8:
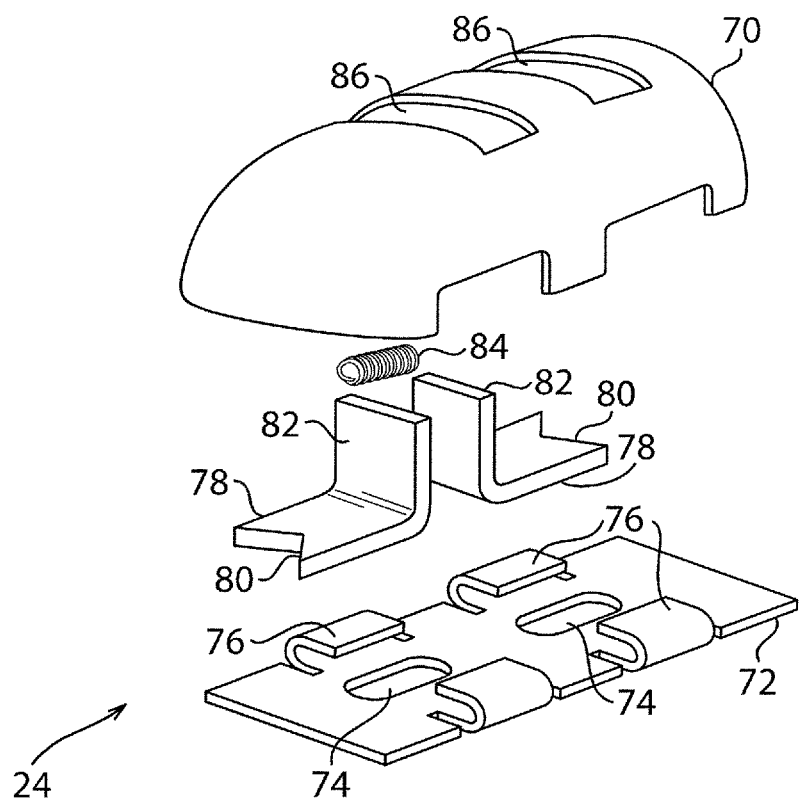
FIG. 8 is a separated perspective of a female piece of a first embodiment of the present invention.
Figure 9:
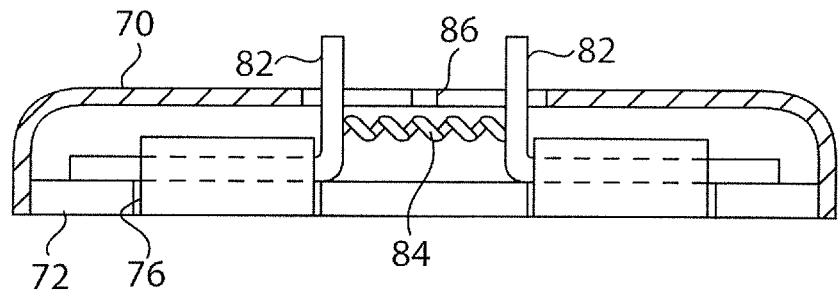
FIG. 9 is a cross section of the female piece of the first embodiment showing latches in a latched position.
Figure 10:
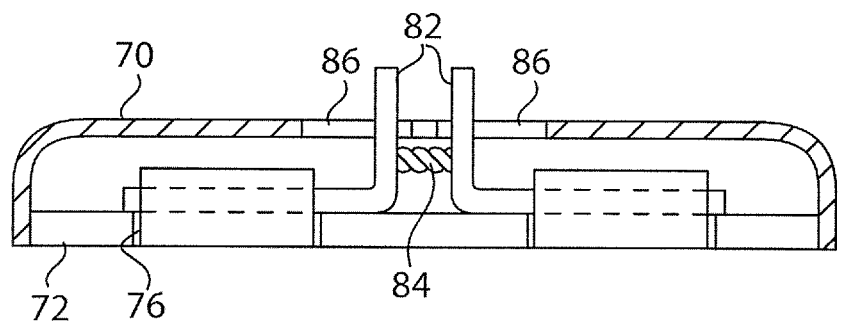
FIG. 10 is a cross section of the female piece of the first embodiment showing latches in an unlatched position.

FIG. 8 illustrates a female piece 24 separated so that each component is visible. The female piece 24 includes a cover 70 that fastens to a base 72. The base 72 includes openings 74 into which the needles 38, 40 of the male piece 22 are inserted when the male piece is joined to the female piece 24. A clip 76 is formed on each side of the base 72 adjacent the openings 74. Two clasps 78 are slideably fastened to the base 72 so that each clasp is held against the base by one pair of opposing clips 76. Each clasp 78 includes a V-shaped opening 80 that releasably secures the needles 38, 40 in position when they are inserted in the openings 74 in the base 72 as shown in FIG. 1. As further illustrated in FIG. 8, each clasp 78 includes an upward extending flange 82 that may be grasped to move the clasps from the latched position as shown in FIG. 9 to the unlatched position as shown in FIG. 10 to disengage the clasps from the needles 38, 40 to allow the male piece 22 to be separated from the female piece 24. A spring 84 is captured between the flanges 82 of the clasps 78 to bias the clasps toward the latched position. The cover 70 includes openings 86 for providing access to the flanges 82 of the clasps 78. Although the female piece 24 may be made of other materials without departing from the scope of the present invention, in one embodiment the female piece is made entirely from titanium sheet material having a stock thickness of between about 0.010 inch and about 0.020 inch. Although the female piece 24 may have other dimensions without departing from the scope of the present invention, in one embodiment the fully assembled female piece has a length of between about 0.4 inch and about 0.7 inch and a width of between about 0.2 inch and about 0.4 inch. Because the female piece 24 is formed using conventional manufacturing techniques, they will not be described in further detail. The cover 70 is held in position on the base 72 using conventional techniques such as brazing, adhesive bonding or by an interference fit.

Figure 11:
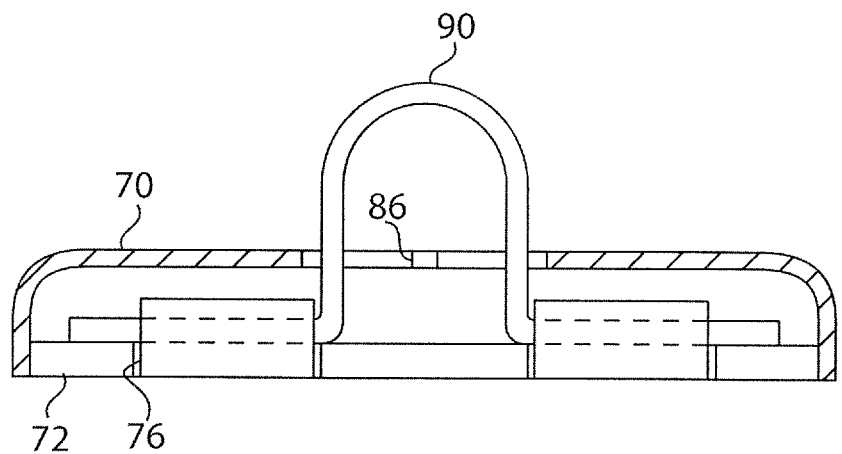
FIG. 11 is a cross section of a female piece of a second embodiment.

In an alternate embodiment illustrated in FIG. 11, the clasps are joined by a curved band 90 so the clasps 72 are formed as one piece. In this alternate embodiment, the band 90 biases the clasps toward the latched positioned and thus replaces the spring. As shown in FIG. 12, each needle (e.g., needle 38) includes notches 92 on opposite sides adjacent its respective tip. As will be appreciated by those skilled in the art, the notches 92 engage a corresponding opening 80 at the outer end of the respective clasp 78 to prevent the needle of the male piece 22 from separating inadvertently from the female piece 24.

FIG. 13 illustrates an instrument, generally designated by 100, for installing the fastener 20 of the present invention into tissue T. The instrument 100 is generally conventional and operates like the instrument described in U.S. Patent Publication No. 2004/0059354 except that one jaw 102 of the instrument includes stabilizing pins 104 that engage the needles 38, 40 of the male piece 22 to hold the male piece in the deployed position so its needles can engage the female piece 24. The jaw 102 also includes a recess 106 for receiving the knuckles 58 of the male piece 22. Because the instrument 100 is conventional in other aspects, it will not be described in further detail.

Although the fastener 20 may have other dimensions without departing from the scope of the present invention, in one embodiment the fastener sized for passing through a patient's esophagus. For example, in one embodiment the male piece 22 has a maximum dimension of between about 0.4 inch and about 0.7 inch when in the collapsed position. In this embodiment, the female piece 24 has a length of between about 0.4 inch and about 0.7 inch, a width of between about 0.2 inch and about 0.4 inch, and a height of between about 0.1 inch and about 0.2 inch. The coupled fastener 20 of this embodiment has a length of between about 0.4 inch and about 0.7 inch, a width of between about 0.2 inch and about 0.4 inch, and a height of between about 0.2 inch and about 0.3 inch plus the thickness of the tissue captured between the male and female pieces.

As mentioned previously, a generally conventional instrument such as partially shown in FIG. 13 may be used to install the fastener 20 of the present invention. The male and female pieces 22, 24 of the fastener 20 are positioned on opposite sides of tissue T to be fastened. The instrument holds the needles 38, 40 of the male piece 22 in the deployed position as shown in FIG. 13 so the needles can pierce the tissue T and extend into the holes 74 of the base 72 of the female piece 24 (FIG. 8). As will be appreciated by those skilled in the art, the applicator pushes the needles 38, 40 through the tissue and into the holes 74 in the base 72 of the female piece 24. When the needles 38, 40 are inserted in the holes 74 in the base 72, the slide cover 104 and cover 70 of the female piece 24 cover the sharp points 42, 44 of needles so they will not penetrate or injure adjacent tissue in the patient. Further, the notches 92 of the needles 38, 40 engage the corresponding openings 80 at the outer ends of the respective clasps 78 to prevent the needles of the male piece 22 from separating from the female piece 24.

In one embodiment, the needles 38, 40 are straight as shown. However, in an alternative embodiment the needles are curved. As will be appreciated by those skilled in the art, the needles 38, 40 travel along arcs as the applicator pushes the needles through the tissue T and into the holes 74 in the base 72 of the female piece 24. Because the arcs through which the needles 38, 40 travel correspond to their overall shape in this alternative embodiment, the needles follow their respective points 42, 44 and do not stretch or tear the tissue as the travel along their arced path.

In one embodiment, the needles 38, 40 may include a series of notches including notch 92 spaced along each needle to permit the base 30 of the male piece 22 and the base 72 of the female piece 24 to be spaced at several different distances relative to each other when the fastener 20 is fastened to tissue. Moreover, the bases 30, 84 may be angled relative to each other so that one needle is inserted farther into the female piece 24 than the other needle. This permits the fastener 20 to accommodate various configurations of tissue. As a result of this adjustability, a desired force can be applied to tissue between the pieces 22, 24 whether or not the tissue has a uniform thickness. Accordingly, force can be limited to prevent tissue necrosis.

After the male and female pieces 22, 24 have been locked together, they may be unlocked and separated from each other. To unlock the fastener 20, the flanges 82 of the latches 78 are pressed toward each other to the unlatched position. As the flanges 82 are pressed toward the unlatched position, the latches 78 disengage the slots 92 so the pieces 22, 24 can be pulled apart. It is envisioned that the fastener 20 can be unlocked, separated and retrieved from the patient using a standard endoscopic snare device (not shown). The snare device is looped around the latch flanges 82. As the snare loop is pulled, the snared parts are pulled toward each other by decreasing the size of the snare loop. As discussed above, the needles 38, 40 are spring-biased to move toward the collapsed positioned shown in FIG. 3 when not retained against the bias. This operates to prevent injury to the patient when the pieces 22, 24 are unlocked and separated, or if the male piece 22 inadvertently becomes separated from the applicator or from the female piece 24. Given the size of the pieces 22, 24 and the protection of sharps from exposure to the patient, the pieces may be safely passed through the gastrointestinal system.

It is recognized that various other configurations can be used for locking the female piece 24 relative to the needles 38, 40 of the male piece 22. Examples of alternative configurations are included in U.S. Patent Publication No. 2004/0059354.

When introducing elements of the present invention or the preferred embodiment(s) thereof, the articles "a", "an", "the" and "said" are intended to mean that there are one or more of the elements. The terms "comprising", "including" and "having" are intended to be inclusive and mean that there may be additional elements other than the listed elements.

As various changes could be made in the above constructions without departing from the scope of the invention, it is intended that all matter contained in the above description or shown in the accompanying drawings shall be interpreted as illustrative and not in a limiting sense.

What is claimed is:

1. A surgical fastener for fastening tissue, the fastener comprising:
   a male fastener comprising;
      a first piece of sheet material formed to have a generally planar base and an elongate first needle portion extending upward from the base; and
      a second piece of sheet material formed to have a generally planar base and an elongate second needle portion extending upward from the base, the second piece of sheet material being pivotally connected to the first piece of sheet material in a manner biasing the second needle of the second piece toward the first needle of the first piece; and
   a female fastener shaped and dimensioned for engagement with the respective first and second needles of the first piece and the second piece, wherein the female fastener includes a spring biased first latch including a flange and an opening shaped and dimensioned for engaging the first needle, a spring biased second latch including a flange and an opening shaped and dimensioned for engaging the second needle, and a spring positioned between the flange of the first latch and the flange of the second latch for biasing the first latch and the second latch in opposite directions.

2. The fastener as set forth in claim 1 wherein:
   the elongate first needle of the first piece is integrally formed with its respective base; and
   the elongate second needle of the second piece is integrally formed with its respective base.

3. The fastener as set forth in claim 1 wherein:
   the base of the first piece includes a first knuckle and the base of the second piece include a second knuckle; and
   the first knuckle and second knuckles of the bases of the first and second pieces, respectively, are joined by a hinge pin.

4. The fastener as set forth in claim 3 wherein the hinge pin biases the bases of the first piece and the second pieces so corresponding tips of the first and second needles of the respective first piece and the second piece are biased toward each other.

5. The fastener as set forth in claim 4 wherein the tips of the first and second needles of the respective first piece and the second piece touch when unimpeded against the bias of the hinge pin.

6. The fastener as set forth in claim 1 wherein:
   the first piece of sheet material is formed to have a shape; and
   the second piece of sheet material is formed to have a shape identical to that of the first piece of sheet material.

* * * * *